United States Patent [19]

Griengl et al.

[11] Patent Number: 5,714,356
[45] Date of Patent: *Feb. 3, 1998

[54] ENZYMIC PROCESS FOR PREPARING ALIPHATIC S-CYANOHYDRINS

[75] Inventors: Herfried Griengl; Nongyuan Shi; Ulrike Pichler; Norbert Klempier, all of Graz; Peter Pöchlauer, Linz, all of Austria

[73] Assignee: DSM Chemie Linz GmbH, Linz, Austria

[*] Notice: The term of this patent shall not extend beyond the expiration date of Pat. No. 5,346,816.

[21] Appl. No.: 491,393

[22] Filed: Jun. 19, 1995

Related U.S. Application Data

[63] Continuation of Ser. No. 252,108, Jun. 1, 1994, abandoned.

[30] Foreign Application Priority Data

Jun. 1, 1993 [AT] Austria ............... 1055/93

[51] Int. Cl.$^6$ ........................... C12P 13/00
[52] U.S. Cl. ..................... 435/128; 435/280
[58] Field of Search ..................... 435/128, 280

[56] References Cited

U.S. PATENT DOCUMENTS

| | | | |
|---|---|---|---|
| 4,859,784 | 8/1989 | Effenberger et al. | 549/491 |
| 5,008,192 | 4/1991 | Neidermeyer et al. | 435/128 |
| 5,122,462 | 6/1992 | Miethe et al. | 435/128 |
| 5,177,242 | 1/1993 | Andruski et al. | 435/128 |
| 5,346,816 | 9/1994 | Griengl | 435/128 |

OTHER PUBLICATIONS

Chem. Abst., vol. 113, col. 131665v (1990).
Effenberger et al., Tetrahedron Lett. 31(9), 1249–52 (1990).
Chem. Abst., vol. 112, col. 234922k (1990).
International Symposium on Enzymes in Organic Synthesis (Indian J. Chem. Sect. B ORG Chem. incl. med–Chem. 32, 1, 1993, 16–19).
Selmar et al., Physiolgia Plantarum, 75, 97–101 (1989).
Selmar et al., Anal. Biochem., 166, 208–211 (1987).
Asada et al., Makromol. Chem., 186, 1755–1762 (1985).
Schurig et al., Angew. Chem., 102, 969–986 (1990).
Chem. Abst. vol. 118, col. 163796h (1993).
Van Scharrenburg et al., Indian Journal of Chemistry, vol. 32B, pp. 16–19, Jan. 1993.
Chem. Abst., vol. 116, col. 126915j (1992).

*Primary Examiner*—Irene Marx
*Attorney, Agent, or Firm*—Wenderoth, Lind & Ponack

[57] ABSTRACT

Process for preparing (S)-cyanohydrins by reacting aldehydes or asymmetrical, aliphatic ketones with hydrocyanic acid in the presence of the (S)-oxynitrilase from *Hevea brasiliensis* at temperatures of up to at most 10° C.

6 Claims, No Drawings

ENZYMIC PROCESS FOR PREPARING ALIPHATIC S-CYANOHYDRINS

This application is a continuation of now abandoned application, Ser. No. 08/252,108, filed Jun. 1, 1994.

Cyanohydrins are of importance, for instance, for synthesizing alpha-hydroxy acids, alpha-hydroxy ketones and beta-amino alcohols which are used for obtaining biologically active substances, for example pharmaceutical active compounds and vitamins, and also pyrethroidal compounds.

A cyanohydrin can be prepared by the addition of a cyanide group to the carbonyl carbon of an aldehyde or of an assymmetrical ketone, resulting in the production of enantiomeric mixtures of optically active cyanohydrins.

Since, normally, only one of the two enantiomers is biologically active in a biologically active enantiomeric mixture, there has been no lack of attempts to find a process for preparing the S-enantiomer of an optically active cyanohydrin in as high a degree of optical purity as possible.

Thus, Makromol. Chem. 186, (1985), 1755–62 describes a process for obtaining S-cyanohydrins by reacting aldehydes with hydrocyanic acid in the presence of benzyloxycarbonyl-(S)-phenylalanine-(S)-histidine methyl ester as the catalyst. However, the optical purity of the resulting S-cyanohydrins is very unsatisfactory.

EP-A-O 326 063 describes an enzymic process for preparing optically active (R)- or (S)-cyanohydrins by reacting aliphatic, aromatic or heteroaromatic aldehydes or ketones with hydrocyanic acid in the presence of (R)-oxynitrilase (4.1.2.10) from *Prunus amygdalis* or oxynitrilase (4.1.2.11) from *Sorghum bicolor*. No examples are given of the stereospecific preparation of aliphatic (S)-cyanohydrins. This is not surprising, since research workers named in EP-A-O 326 063 indicate Angew. Chemie 102 (1990), No.4, pp 423–425 that Sorghum bicolor (S)-oxynitrilase cannot be used for preparing aliphatic S-cyanohydrins from hydrocyanic acid. This finding is also confirmed by F. Effenberger et al. in Tetrahedron Letters Vol. 31, No. 9 (199), pp. 1249–1252.

It has now been found, unexpectedly, that it is indeed possible to convert aliphatic aldehydes or asymmetrical aliphatic ketones into S-cyanohydrins in a stereospecific manner using hydrocyanic acid and oxynitrilase if the (S)-oxynitrilase from *Hevea brasiliensis* is employed as the enzyme and the reaction is carried out at temperatures of up to at most 10° C.

The invention therefore relates to an enzymic process for preparing aliphatic (S)-cyanohydrins, which process is characterized in that an aliphatic aldehyde or an asymmetrical aliphatic ketone is reacted with hydrocyanic acid in a diluent in the presence of the (S)-oxynitrilase from *Hevea brasiliensis* at temperatures of up to at most 10° C.

In the process according to the invention, an aliphatic aldehyde or an asymmetrical aliphatic ketone, hydrocyanic acid, *Hevea brasiliensis* oxynitrilase and a diluent are employed as the starting materials. In this context, aldehydes are understood to mean saturated or unsaturated aliphatic, straight-chain, branched or cyclic aldehydes. The process is particularly suited for converting straight-chain aldehydes having, in particular, 2 to 18 C atoms, preferably from 2 to 12, which are saturated or unsaturated once or more than once. The aldehyde can have C—C double bonds or C—C triple bonds. The aldehyde can be unsubstituted or be substituted by groups which are inert under the reaction conditions, for example by optionally substituted aryl or heteroaryl groups, such as phenyl or indolyl groups, and by halogen, ether, alcohol, acyl, carboxylic acid, carboxylic ester, nitro or azido groups. The aldehyde is preferably unsubstituted.

Ketones are understood to mean saturated or unsaturated, straight-chain, branched or cyclic ketones. In this context, ketones are preferred which are sterically hindered as little as possible at one end, in particular methyl ketones. The ketones may be saturated or unsaturated once or more than once. They can be unsubstituted or substituted by groups which are inert under the reaction conditions, for example by optionally substituted aryl or heteroaryl groups, such as phenyl or indolyl groups, or by halogen, ether, alcohol, acyl, carboxylic acid, carboxylic ester, nitro or azido groups.

Hydrocyanic acid is employed as the cyanide group donor. The hydrocyanic acid can be conducted in as a gas, or employed in the form of one of its salts, such as NaCN or KCN, from which it is released in situ during the course of the reaction as a consequence of the given reaction conditions.

The S-oxynitrilase from *Hevea brasiliensis* is used as the oxynitrilase. It can be employed in the purified or unpurified form, and as such or immobilized. It can be prepared and purified by, for example, precipitating with ammonium sulfate and subsequently dialyzing, for instance in accordance with D. Selmar et al., Physiologia Plantarium 75 (1989), 97–101.

The reaction is effected in a diluent. It has proved to be particularly advantageous that the reaction can be carried out in an aqueous diluent in the absence of organic solvents, which can rapidly inhibit the activity of the enzyme, without, which was not to be expected, any racemization of the product taking place. However, the reaction according to the invention can also be effected in an organic diluent or in the presence of an organic solvent for the aldehyde or the ketone, where appropriate in a two-phase system, for example in an ultrafiltration reactor. Aliphatic or aromatic hydrocarbons, which are optionally halogenated, and alcohols, ethers or esters can be used as organic diluents or solvents. Organic solvents which are not miscible with water, such as, for example, aliphatic or aromatic hydrocarbons, which are optionally halogenated, and ethers or esters can be employed as the organic solvent for the aldehyde or the ketone in a two-phase system. Preferably, the reaction is effected in an aqueous diluent and not in the presence of an organic solvent. Water, or an aqueous solution of salt or buffer, is employed as the aqueous diluent. Preferably, an aqueous solution of buffer is used, very preferably one which contains sodium citrate. In this context, the pH should be less than 7, preferably from about 3 to 5.

Approximately 1,500 to 15,000 g of diluent and from $10^4$ to $10^6$ IU of oxynitrilase activity, preferably from about $10^5$ to $5.10^5$ IU, are added per mol of aldehyde or ketone. In this context, one IU (international unit) expresses the formation of one micromol of product per minute and per gram of crude enzyme isolate. The quantity of oxynitrilase required is best determined in an activity test, for instance in accordance with Selmar et al., Analytical Biochemistry 166 (1987), 208–211.

At least 1 mol, preferably from 1 to 3 mol, of hydrocyanic acid are added per mol of aldehyde group or keto group employed. When a salt is added, the hydrocyanic acid is liberated from the salt as a consequence of the pH, which is less than 7.

The reaction mixture is shaken or stirred at temperatures of from about −5° to 10° C. It has turned out, unexpectedly, that the oxynitrilase is best employed in a temperature range of from −5° to 5° C. Under these circumstances, the enzyme exhibits virtually no loss of activity, in spite of the low temperature.

In the reaction, the cyanide group of the hydrocyanic acid is transferred to the carbonyl carbon atom of the aldehyde or ketone employed, and the S-enantiomer of the optically active cyanohydrin corresponding to the aldehyde or ketone employed is produced in the main. The progress of the reaction is monitored by gas chromatography, for example.

Once the reaction is complete, the cyanohydrin which has been formed can be extracted from the reaction mixture with the aid of an organic solvent which is not miscible with water, for instance aliphatic or aromatic, optionally halogenated, hydrocarbons, e.g. pentans, hexane, toluene, xylols, methylene chloride, ethers, such as, for instance, diethyl ether, diisopropyl ether or methyl tert-butyl ether, or esters, for example ethyl acetate, or mixtures of such solvents. If the extracted product is insufficiently pure, a purification operation can follow. The purification can be effected by a known method, and is most successful when chromatography is used.

In a preferred embodiment, approximately 100 mg of aldehyde or ketone are shaken or stirred in a closed system in from 15 to 30 g of an aqueous solution of buffer, which has a pH of about 4 and contains sodium citrate, together with 2 mol of hydrocyanic acid per mol of aldehyde group or keto group employed and from $10^5$ to $5.10^5$ IU of *Hevea brasiliensis* oxynitrilase activity at temperatures of from 0° to 5° C. The progress of the reaction is monitored by gas chromatography. Once the reaction is finished, the reaction mixture is extracted with methylene chloride, and the organic phase then dried and evaporated off. The residue can be further purified by column chromatography.

In the way and manner described, optically active S-enriched cyanohydrins are obtained, in a simple manner and for the first time, from aliphatic aldehydes or asymmetrical aliphatic ketones by reaction with hydrocyanic acid in good yields and with a high degree of purity. The process therefore represents an enrichment of the art.

EXAMPLE 1

500 IU of crude enzyme preparation from *Hevea brasiliensis* were suspended in 20 ml of 0.5N sodium citrate buffer, pH=3.75, 200 mg of hexanal (2 mmol) were added, and the mixture was cooled to 0° C. Subsequently, 260 mg of KCN (4 mmol) dissolved in 20 ml of 0.5N sodium citrate buffer, pH=3.75, were added dropwise, while stirring, within the space of 30 minutes. After completion of the reaction, which was ascertained by gas chromatography, the aqueous phase was extracted twice with 25 ml of methyl tert-butyl ether on each occasion, and the combined organic phases were dried over $Na_2SO_4$ and evaporated off. The residue was chromatographed through silica gel using petroleum ether: ethyl acetate=4:1. This yielded 0.22 g, that is 86% of theory, of S-hexanalcyanohydrin having an $[\alpha]_D^{20}=-13.4°$, corresponding to an optical purity (ee) of 92%. The optical purity was determined in accordance with V. Schuring et al., Ang. Chemie 102 (1990), 969–986 by gas-chromatographic analysis of the cyanohydrin, which was derivatized with (S)-menthyl chloroformate, on a polysiloxane separation column (30 m×0.25 mm, 86% polydimethylsiloxane, 7% cyanopropylsiloxane and 7% phenylsiloxane).

The derivatization was carried out as follows: 5–10 mg of the hexanalcyanohydrin were combined with a 3-molar excess of (S)-menthyl chloroformate and pyridine in dry methylene chloride in a derivatization vessel, and the mixture was analyzed by gas chromatography after 10 minutes.

EXAMPLE 2

In correspondence with Example 1, 68 mg (1 mmol) of propenal were reacted with 130 mg (2 mmol) of KCN and 200 IU of crude enzyme preparation from *Hevea brasiliensis* in a total of 15 ml of 0.5N sodium citrate buffer, pH 3.75. The propenalcyanohydrin was isolated after 2 hours as described in Example 1. This yielded 0.029 g, that is 38% of theory, of (S)-propenalcyanohydrin having a $[\alpha]_D^{20}=+4.9$, corresponding to an optical purity (ee) of 91%.

EXAMPLE 3

In correspondence with Example 1, 196 mg (2 mmol) of 2-(E)-hexenal were reacted with 260 mg (4 mmol) of KCN and 700 IU of crude enzyme preparation from *Hevea brasiliensis* in a total of 25 ml of 0.5N sodium citrate buffer, pH 3.75. The 2-(E)-hexenalcyanohydrin was isolated after 2 hours as described in Example 1. This yielded 0.043 g, that is 17% of theory, of (S)-2-(E)-hexenalcyanohydrin having a $[\alpha]_D^{20}=+20.3$, corresponding to an optical purity (ee) of 96%.

EXAMPLE 4

In correspondence with Example 1, 144 mg (1.5 mmol) of 2-hexynal were reacted with 195 mg (3 mmol) of KCN and 600 IU of crude enzyme preparation from *Hevea brasiliensis* in a total of 25 ml of 0.5N sodium citrate buffer, pH 3.75. The 2-hexynalcyanohydrin was isolated after 3 hours as described in Example 1. This yielded 0.081 g, that is 43% of theory, of (S)-2-hexynalcyanohydrin, having a $[\alpha]_D^{20}=-20.4$, corresponding to an optical purity (ee) of 80%.

EXAMPLE 5

In correspondence with Example 1, 98 mg (1.4 mmol) of 2-(E)-butenal were reacted with 182 mg (2.8 mmol) of KCN and 200 IU of crude enzyme preparation from *Hevea brasiliensis* in a total of 20 ml of 0.5N sodium citrate buffer, pH 3.75. The 2-(E)-butenalcyanohydrin was isolated after 3 hours as described in Example 1. This yielded 0.038 g, that is 28% of theory, of (S)-2-(E)-butenalcyanohydrin, having a $[\alpha]_D^{20}=+29.4$, corresponding to an optical purity (ee) of 87%.

EXAMPLE 6

2-Pentanone (3.0 mmol, 258 mg) and crude enzyme preparation from *Hevea brasiliensis* (168 mg, 200 IU) were suspended in 0.1M sodium citrate (pH, 3.75, 5 ml). While cooling in ice, a solution of potassium cyanide (6.0 mmol, 391 mg) in 0.1M citric acid (50 ml) was added dropwise over a period of 20 min., and after that the mixture was adjusted to pH 4 with 0.1M citric acid. The reaction solution was stirred for 3.5 h while cooling in ice, and then extracted with diethyl ether followed by drying over $Na_2SO_4$. After the solvent had been distilled off, the residue was purified by chromatography (silica gel, ethyl acetate/benzine 1/6). 100 mg (30%) of (S)-2-hydroxy-2-methylpentanenitrile were obtained. ee: 75%. $[\alpha]_D^{20}=-2.5°$ (c=2, $CHCl_3$).

EXAMPLE 7

In an anlogous manner, 144 mg, that is 30% of theory, of (S)-2-hydroxy-2,3-dimethylbutanenitrile were obtained from 3-methyl-2-butanone (4.1 mmol, 352 mg), crude enzyme preparation from *Hevea brasiliensis* (200 IU, 168 mg), KCN (8.4 mmol, 546 mg), Na citrate (0.1M, pH-3.75, 5 ml) and citric acid (0.1M, 55 ml). ee: 82%. $[\alpha]_D^{20}=+1.6°$ (c=2, $CHCl_3$).

What we claim is:

1. An enzymatic process for the preparation of an aliphatic (S)-cyanohydrin, which comprises reacting a straight-chain, saturated or unsaturated aliphatic aldehyde having from 2 to 12 carbon atoms or a straight-chain, saturated or unsaturated aliphatic methylketone having from 4 to 12 carbon atoms with hydrocyanic acid in a diluent, using as a catalyst (S)-oxynitrilase from *Hevea brasiliensis*, at a temperature of up to at most 10° C., to form a reaction mixture containing said aliphatic (S)-cyanohydrin and isolating said aliphatic (S)-cyanohydrin from the reaction mixture.

2. The process according to claim 1, wherein from 2 to 3 moles of hydrocyanic acid are employed per mole of aldehyde or ketone.

3. The process according to claim 1, wherein said diluent is an aqueous solution of buffer.

4. The process according to claim 1, comprising carrying out the reaction at a temperature of from −5° C. to +5° C.

5. The process according to claim 1, comprising carrying out the reaction in the presence of from $10^4$ to $10^6$ IU of the (S)-oxynitrilase from *Hevea brasiliensis* per mole of aldehyde or ketone.

6. The process according to claim 1, wherein said diluent is an aqueous or organic solvent.

* * * * *